(12) United States Patent
Dalal et al.

(10) Patent No.: US 10,245,347 B2
(45) Date of Patent: *Apr. 2, 2019

(54) ELASTOMER COMPOSITION COMPRISING POLYOLEFIN ELASTOMERS

(71) Applicant: The Procter & Gamble Company, Cincinnati, OH (US)

(72) Inventors: Urmish Popatlal Dalal, Milford, OH (US); Ray Dennis Dria, Mason, OH (US); David Harry Melik, Cincinnati, OH (US); Keith Richard Coburn, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/803,949

(22) Filed: Nov. 6, 2017

(65) Prior Publication Data
US 2018/0055967 A1 Mar. 1, 2018

Related U.S. Application Data

(63) Continuation-in-part of application No. 14/708,344, filed on May 11, 2015, now Pat. No. 9,834,667.

(60) Provisional application No. 62/008,464, filed on Jun. 5, 2014.

(51) Int. Cl.
| | |
|---|---|
| C08L 23/12 | (2006.01) |
| A61L 15/22 | (2006.01) |
| C08L 23/16 | (2006.01) |
| B32B 27/08 | (2006.01) |
| B32B 27/32 | (2006.01) |
| C08J 5/18 | (2006.01) |
| B32B 5/02 | (2006.01) |
| B32B 27/12 | (2006.01) |
| B32B 25/12 | (2006.01) |
| B32B 27/18 | (2006.01) |
| B32B 27/20 | (2006.01) |

(52) U.S. Cl.
CPC ............ *A61L 15/225* (2013.01); *B32B 5/022* (2013.01); *B32B 25/12* (2013.01); *B32B 27/08* (2013.01); *B32B 27/12* (2013.01); *B32B 27/18* (2013.01); *B32B 27/20* (2013.01); *B32B 27/32* (2013.01); *B32B 27/327* (2013.01); *C08J 5/18* (2013.01); *C08L 23/12* (2013.01); *C08L 23/16* (2013.01); *B32B 2255/00* (2013.01); *B32B 2255/02* (2013.01); *B32B 2262/12* (2013.01); *B32B 2270/00* (2013.01); *B32B 2307/51* (2013.01); *B32B 2307/54* (2013.01); *B32B 2307/724* (2013.01); *B32B 2437/00* (2013.01); *B32B 2535/00* (2013.01); *B32B 2555/00* (2013.01); *C08J 2323/12* (2013.01); *C08J 2323/14* (2013.01); *C08J 2323/16* (2013.01); *C08J 2423/14* (2013.01); *C08J 2423/16* (2013.01); *C08L 2203/02* (2013.01); *C08L 2203/16* (2013.01); *C08L 2205/025* (2013.01); *C08L 2205/03* (2013.01); *C08L 2205/035* (2013.01); *Y10T 428/31938* (2015.04)

(58) Field of Classification Search
CPC ......... B32B 5/022; B32B 27/12; B32B 27/32; B32B 25/12; B32B 27/18; B32B 27/20; B32B 27/08; B32B 2255/02; B32B 2307/51; B32B 2262/12; B32B 2555/00; B32B 2437/00; B32B 2535/00; B32B 2255/00; B32B 2270/00; B32B 2307/54; B32B 2307/724; C08J 5/18; C08J 2323/08; C08J 2323/14; C08J 2423/08; C08J 2323/16; C08J 2323/12; A61L 15/225; C08L 23/16; C08L 23/12; C08L 25/08; C08L 2203/16; C08L 2203/02; C08L 2205/035; C08L 2205/03; C08L 2205/025; Y10T 428/31938
See application file for complete search history.

(56) References Cited

U.S. PATENT DOCUMENTS

| | | | |
|---|---|---|---|
| 6,120,487 A | 9/2000 | Ashton | |
| 6,169,151 B1 | 1/2001 | Waymouth et al. | |
| 6,518,378 B2 | 2/2003 | Waymouth et al. | |
| 6,555,643 B1 | 4/2003 | Rieger | |
| 6,559,262 B1 | 5/2003 | Waymouth et al. | |
| 9,834,667 B2 * | 12/2017 | Dalal et al. ............. | C08L 23/14 |

(Continued)

FOREIGN PATENT DOCUMENTS

| | | |
|---|---|---|
| EP | 1256594 A1 | 11/2002 |
| WO | WO 2007/053603 | 5/2007 |

OTHER PUBLICATIONS

International Search Report, PCT/US2015/030067, dated Jul. 3, 2015, 9 pages.

(Continued)

*Primary Examiner* — Nathan M Nutter
(74) *Attorney, Agent, or Firm* — Andrew J. Hagerty

(57) ABSTRACT

Disclosed is an elastomer composition comprising polyolefin elastomer material which exhibits improved hysteresis properties, said elastomer composition having the following properties:

(1) an average integrated enthalpy sum of no greater than 17 J/g according to the Thermal Analysis Method defined herein;
(2) an average integrated enthalpy ratio of from 0.6 to 300 according to the Thermal Analysis Method defined herein;
(3) an unload stress at 75% strain of above 0.8 MPa according to the Hysteresis Test defined herein; and
(4) a load stress/unload stress ratio at 75% strain of 1 to 2.6 according to the Hysteresis Test defined herein.

20 Claims, 8 Drawing Sheets

(56) References Cited

U.S. PATENT DOCUMENTS

2005/0171285 A1    8/2005   Cozewith et al.
2015/0353719 A1    12/2015  Dalal et al.

OTHER PUBLICATIONS

Jiang, Genjie, et al., "Improved Processing Behaviors and Mechanical Properties of Polyolefin Elastomer Blends Prepared by Ultrasound-Assisted Extrusion", Journal of Applied Polymer Science, vol. 112, 2136-2142 (2009), XP-002741087.

* cited by examiner

ELASTOMER COMPOSITION COMPRISING POLYOLEFIN ELASTOMERS

FIELD OF THE INVENTION

The present invention relates to an elastomer composition comprising polyolefin elastomer which exhibits improved hysteresis properties.

BACKGROUND OF THE INVENTION

Elastic materials, especially elastic films, are commonly used for a wide variety of applications. For example, absorbent articles typically include one or more components that rely on film materials, especially elastic film materials, to control the movement of liquids and to provide a comfortable, conforming fit when the article is worn by a wearer. A typical way of introducing elastic material in an absorbent article is either though waistbands, leg elastics, side panels, elastic belts, stretch outer cover or stretch ears. Hysteresis behavior, i.e. the load to unload performance in tensile testing, is a good measure of how well the product performs and it is often associated with the elastic materials used in the article.

Conventional elastic film materials made out of styrenic block copolymers and/or polyurethanes may provide favorable hysteresis performance, but may also undesirably impact the cost and/or complexity of manufacturing the product. With recent metallocene chemistry development, a new class of elastic polyolefins including, but not limited to random copolymerized propylene with ethylene, have become available for product application, such as described in US Patent Application publication US 2005/0171285A and PCT Patent Publication WO 2007/053603. While these materials deliver certain hysteresis performance, there is yet room for improvement, without significant cost added for making the material.

SUMMARY OF THE INVENTION

Figure 1:
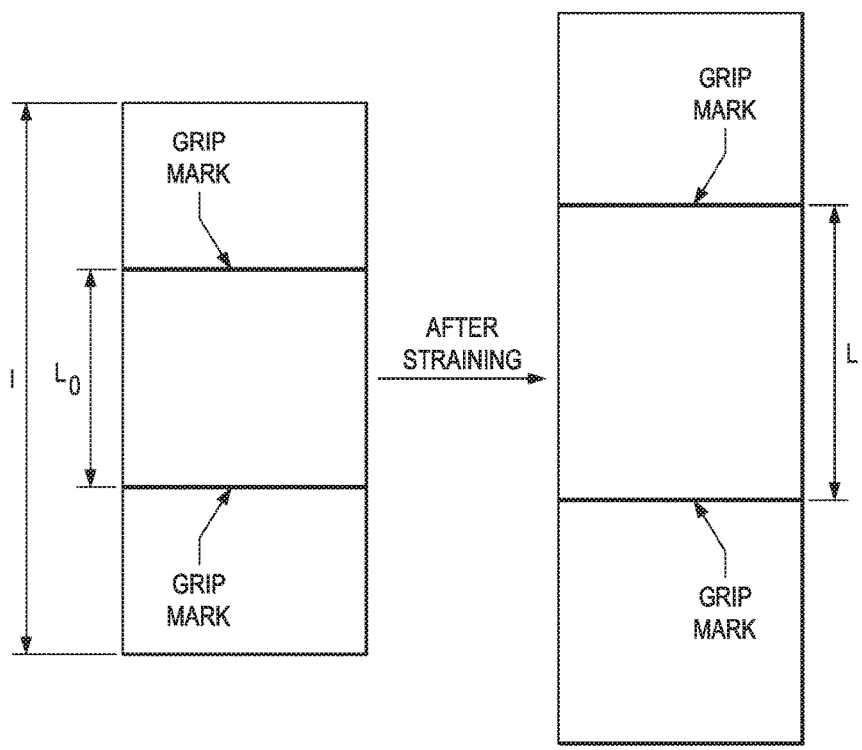
FIG. 1 is a systematic representation of the measurement methods for the Initial Tensile Test and the Hysteresis Test defined herein.

In order to provide a solution to the opportunity for improvement set forth above, an elastomer composition which comprises polyolefin elastomers is disclosed. The composition exhibits suitable hysteresis properties as well as acceptable robustness to tensile stress without significant cost added for making the material.

DETAILED DESCRIPTION OF THE INVENTION

Definitions

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the material in the direction of activation. Activation of a laminate that includes an elastic material joined to a plastically extensible material typically results in permanent deformation of the plastically extensible material, while the elastic material returns substantially to its original dimension. "Activate", and variations thereof, means subjecting a material to an activation process.

"Aperture" means an opening in a film purposefully added during film making or laminate making, which is intended to impart a desired characteristic such as breathability. "Basis weight" is the property of a sheet or web of material calculated as the mass of the material divided by its surface area. The units for basis weight herein are grams per square meter ($g/m^2$).

"Breathable" means a film or laminate that has an Air Permeability Value of between 5.0 and 50 $m^3/m^2/min$ according to the Air Permeability Test described below.

"Copolymer" means a polymer derived from two or more monomer species wherein the polymer chains each comprise repeat units from more than one monomer species.

"Crystalline melting temperatures" are determined by Differential Scanning calorimetry, for example, as described below in the Thermal Analysis method. Materials may have one or more melting endotherm peaks.

"Disposed" means an element is positioned in a particular place with regard to another element.

"Extensible" means the ability to stretch or elongate, without rupture or breakage, to at least 130% strain, for example, as described below in the Hysteresis Test.

"Elastic," "elastomeric," and "elastically extensible" mean the ability of a material to stretch by at least 130% strain without rupture or breakage at a given load, and upon release of the load the elastic material or component exhibits at least 70% recovery (i.e., has less than 30% set). For example, an elastic material that has an initial length of 25.4 mm can stretch to at least 58.4 mm (130% stretch) and, upon removal of the force, retract to a length of 30.5 mm (i.e., have a set of 5.1 mm or 20%). Stretch, sometimes referred to as strain, percent strain, engineering strain, draw ratio, or elongation, along with recovery and set may each be determined according to the Hysteresis Test described below. Materials that are extensible but not "elastic" are considered "plastically extensible" materials.

"Film" means a sheet-like material wherein the length and width of the material far exceed the thickness of the material (e.g., 10 times, 50 times, or even 1000 times or more). Films are typically liquid impermeable but may be configured to be breathable.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the film in which it is extruded or the web in a manufacturing process. Directions within 45 degrees of the MD are considered to be machine directional. The "cross machine direction" or "CD" is the direction substantially perpendicular to the MD and in the plane generally defined by the film or web. Directions within 45 degrees of the CD are considered to be cross directional.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" means the state of an element, material or component at rest with substantially no external force acting on the element, other than gravity.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material.

Elastomer Composition

Semi-crystalline, or metallocene polyolefins are widely used in disposable absorbent products. It is known that their performance depends on amount of crystallinity. The crystallinity decreases with decreasing stereo-regularity, and the material shows more elastic behavior. A number of methods are known for controlling crystallinity, such as by introducing stereo-irregularity or by introducing a comonomer. Some homopolyolefins and random copolymers, as well as blends of such random copolymers, known by tradenames Vistamaxx™ available from ExxonMobil and VERSIFY™ from Dow Corning, are synthesized based on this principle, and tend to show elastic performance. While these materials deliver certain hysteresis performance, there is yet room for improvement, without significant cost added for making the material.

The elastomer composition of the present invention may be made by modifying or blending one or more polyolefin elastomer materials that have elastic properties, according to the definition herein. The polyolefin elastomer materials useful herein include, but are not limited to, any polymers or copolymers of polyolefins such as polyethylene and polypropylene. Particularly suitable examples of elastic materials include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regio-irregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and blends or combinations thereof. Suitable polypropylene polymers including crystalline isotactic blocks and amorphous atactic blocks are described, for example, in U.S. Pat. Nos. 6,559, 262, 6,518,378, and 6,169,151. Suitable isotactic polypropylene with stereo-irregularity along the polymer chain are described in U.S. Pat. No. 6,555,643 and EP 1 256 594 A1. Suitable examples include elastomeric random copolymers including propylene with a low level comonomer (e.g., ethylene or a higher alpha-olefin) incorporated into the backbone.

The elastomer composition of the present invention may be made by blending at least two (2) polyolefin elastomer materials. The polyolefin elastomer materials useful for preparing the present elastomer composition in such manner include metallocene polypropylene, and those having a crystalline melting point of at least 75° C., or at least 80° C., as defined by the Thermal Analysis Method defined herein. Such polyolefin elastomer materials may be selected from commercially available material such as, but not limited to: Vistamaxx 6102 (available from ExxonMobil, Houston, Tex.), random propylene-ethylene copolymers; NOTIO PN-0040 and PN-2070 (available from Mitsui Chemicals, Tokyo Japan), elastic polyolefin resins; L-MODU X901S (available from Mitsui Chemicals, Tokyo Japan): a stereo copolymer of polypropylene; Versify 2400A, 2400B, 3401A and 3401 B (available from Dow Chemical, Midland, Mich.), random copolymers of propylene with ethylene.

The elastomer composition of the present invention may include one or more additives commonly used in the art to tailor the composition for a particular use. For example, stabilizers, antioxidants, and bacteriostats may be employed to prevent thermal, oxidative, and bio-chemical degradation of the elastomer composition. Generally, the additive or additives may account for 0.01% to 20%; 0.01% to 10%; or 0.01% to 2% of the total weight of the elastomer composition.

Suitable examples of stabilizers and antioxidants include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2, 4,6-tris(3-5-di-tert-butyl-4-hydroxybenzyl) benzene; pentaerythritol tetrakis-3(3,5-di-tert-butyl-4-hydroxyphenyl)

propionate; n-octadecyl-3(3,5-ditert-butyl-4-hydroxyphenyl) propionate; 4,4'-methylenebis(4-methyl-6-tert butylphenol); 4,4'-thiobis(6-tert-butyl-o-cresol); 2,6-di-tert-butylphenol; 6-(4-hydroxyphenoxy)-2,4-bis(n-ocytlthio)-1,3,5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio)ethyl-3,5-di-tert-butyl-4-hydroxybenzoate; and sorbitol hexa-(3,3,5-di-tert-butyl-4-hydroxy-phenyl) propionate. Proprietary commercial stabilizers and/or antioxidants are avalaible under a number of tradenames including a variety of Wingstay®, Tinuvin® and Irganox® products.

Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation IRGASAN PA from Ciba Specialty Chemical Corporation, Tarrytown, N.Y.

Various viscosity modifiers, processing aids, slip agents or anti-block agents can be employed as additives to provide improved handling characteristics or surface characteristics. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly suitable processing oil is mineral oil.

A variety of fillers can also be used as additives to the elastomer composition. Examples of suitable fillers include talc, calcium carbonate, carbon black, clay, and mica. The filler may be selected in combination with antioxidants to minimize impact on stability.

A wide range of pigments can also be employed to impart desirable color to the elastomer composition. Organic and inorganic pigments such as azo, quinacridone, cadmium, and chrome containing pigments may be blended with the elastomer composition.

Nucleating agents such as sorbitol based compounds, sodium salts of organic phosphates, sodium benzoate may be used in combination with the elastomer composition. They help improve optical properties and physical properties of the elastomer composition.

Compatiblizers can also be used in combination with the elastomer composition. They help improve interfacial adhesion between components. This often results in better mechanical and/or optical properties.

The elastomer composition of the present invention may be used in extrusion processes to produce products, such as fiber or film forms. Fibers may be meltblown and/or spun to form nonwovens. The elastomer composition can be cast or blown to make a sheet. The elastomer composition may be used in combination with other resins, either blended or as separate layers to form fibers or sheets. The elastomer composition of the present invention may also be blow molded or injection molded using techniques available in the industry.

The elastomer composition of the present invention may be formed by any suitable method in the art, for example, by extruding molten thermoplastic and/or elastomeric polymers through a slit die and subsequently cooling the extruded sheet. Other non-limiting examples for making film forms include casting, blowing, solution casting, calendering, and formation from aqueous or, non-aqueous cast dispersions. One suitable method for obtaining the elastomer composition of the present invention in the film form is by allowing polyolefin elastomers or other materials obtained in pellet form to be mixed and extruded by a high torque co-rotating twin-screw extruder, namely extrusion blending. The elastomer composition of the present invention may be made into a film having a basis weight of from about 5 to about 150 $g/m^2$, preferably from about 10 to about 100 $g/m^2$.

The elastomer composition of the present invention preferably has a crystalline melting point of at least 75° C., or at least 80° C., as defined by the Thermal Analysis Method defined herein. Without being bound by theory, it is believed that the elastomer composition of the present invention having such melting point may provide better hysteresis, and further provide better stability at relatively high temperature storage conditions.

According to the Hysteresis Test defined herein, the elastomer composition of the present invention exhibits an unload stress at 75% strain of greater than 0.80 MPa. According to the Hysteresis Test, the elastomer composition of the present invention exhibits a load stress/unload stress ratio at 75% strain of between 1.0 and 2.6. The elastic film of the present invention show desired hysteresis properties at a low basis weight after straining, which is a treatment typically undergone for an elastic element used on a product. Without being bound by theory, it is believed that such properties provide good fit required of, for example, absorbent articles.

According to the Thermal Analysis Method, the elastomer composition of the present invention exhibits characteristic crystalline melting properties when the regions are divided into 3 temperature zones: Zone I between 30-80° C., Zone II between 80-120° C., and Zone III between 120-170° C. Without being bound by theory, it is believed that Zones I and III provide a correlation between crystallinity and hysteresis performance. The elastomer composition of the present invention exhibits an average integrated enthalpy sum of Zones I and III of no greater than 17 J/g, preferably between about 5-17 J/g. Further, the elastomer composition of the present invention has an average integrated enthalpy ratio of Zone I to Zone III of from 0.6 to 300, preferably 0.8 to 300 or still preferably 1.0 to 300.

According to the Initial Tensile test, the elastomer composition of the present invention exhibits a stress at break value of greater than 10 MPa and/or a % strain at break of greater than 500%. By having such high stress at break and/or % strain at break, the elastic film comprising the composition is believed to be tough enough for activation, and exhibit appropriate endurance during processing for making an elastic material, or assembling an article using such elastic film.

The elastic film of the present invention shows desired performance as a mono-layer film, and may be co-extruded with other materials to form a multi-layer film. One or more layers of the multi-layer film can be a skin layer, which helps prevent blocking. The skin layer is preferably made of plastically extensible materials. A layer in the multi-layer film can be provided as a tie layer, which provides good boundary strength with two non-bondable adjacent layers. The elastic film of the present invention may further be apertured to impart breathability.

The elastic film of the present invention having a basis weight of from about 5 to about 150 $g/m^2$ may be laminated with other plastic films, nonwovens, and/or substrates. Such laminates are useful as elastic elements for absorbent articles such as diapers, feminine pads, bibs, linens, pet sheets, wound dressings, hospital gowns, and the like. Elements useful for making with the laminates include, but are not limited to, waistbands, leg elastic, side panels, elastic belts, stretch outer cover or stretch ears.

Test Methods

1. Basis Weight, Initial Tensile Test, and Hysteresis Test 1-1. Sample Preparation If necessary, the product part comprising the elastomer composition (e.g. stretch ear) is cut from the product. If the elastomer composition is bonded or attached to other components, then it is separated from the other components such as laminated nonwoven layers by techniques such as applying "Quik-Freeze®" type cold spray, or other suitable methods that do not permanently alter the properties of the elastomer composition. Care should be taken to prevent stretching of the elastomer composition during the separation process. If the elastomer composition is standalone, it is used as is for further sample preparation. The sample is in the form of a film having a basis weight of between 5 and 150 g/m². If the sample has a greater basis weight than such range, the sample is sliced into an appropriate basis weight.

The direction in which the elastic film will stretch in its intended use is considered the primary stretch direction of the material. For standalone films, where the primary stretch direction is not known, the direction in which the film has greatest extensibility is assumed to be the primary stretch direction. Two sets (Set A and Set B) of specimens are cut. A first set (Set A) of rectilinear specimens at least 30 mm long in the primary stretch direction, and 25.4 mm wide in the perpendicular direction, is cut from the center portion of the product part. Similarly, a second set (Set B) of rectilinear specimens with 25.4 mm width in primary direction and 30 mm length in the perpendicular direction, is cut from the center portion of the identical product part. Articles having areas of film smaller than 30×25.4 mm are considered to be outside the scope of this method. Five specimens are cut from the same portion of identical products for each set. The basis weight of each film specimen is measured. If the difference in the elastic film specimen basis weight is more than 10% between highest and lowest basis weight samples for any set, then specimens are re-collected for that set from a different part of the film, or from fresh products. Each set is analyzed by the methods described below. For the Initial Tensile Test and Hysteresis Test, the direction in which specimen has longer dimension is considered the specimen direction of stretching.

1-2. Specimen Weight and Basis Weight

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{\text{(Weight of the specimen in grams)}}{\text{(Length of the specimen in meter)} \cdot \text{(Width of the specimen in meter)}}$$

1-3. Tensile Test Setup

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the specimen. The load cell is selected so that the forces measured are between 10% and 90% of the capacity of the load cell used. The initial distance between the lines of gripping force (gauge length) is set at 25.4 mm. The load reading on the instrument is zeroed to account for the mass of the fixture and grips.

The specimen is mounted into the grips in a manner such that there is no slack and the load measured is between 0.00 N and 0.02 N. The specimen is mounted in the center of the grips, such that the specimen direction of stretching is parallel to the applied tensile stress.

1-4. Initial Tensile Test

The instrument is set up and the specimen mounted as described in the Tensile Test Setup above. The tensile test is initiated and the specimen is extended at 254 mm/min, with a data acquisition rate of at least 50 Hertz, until the specimen breaks, typically 800-1000% strain. The % Strain is calculated from the length between grip lines L, and initial gauge length, $L_0$, as illustrated in FIG. 1, using the following formula:

$$\% \text{ Strain} = \frac{(L - L_0)}{L_0} \times 100$$

Five specimens of each set are measured, and the arithmetic average of force at 130% strain (N), force at break (N), stress at 130% strain (MPa), stress at break (also called Tensile Strength, MPa), and % Strain at break are recorded. % Strain at break is defined as the % Strain at peak force. Data are generated for Set A and Set B.

Stress in MPa is calculated as follows: Stress=[measured force]/[specimen cross-sectional area].

Specimen cross-sectional area is calculated from specimen weight, W (g); before straining specimen length, l (mm); and density of the material, $\rho$ (g/cm³). Specimen cross-sectional area $A_0$ (mm²) is given by formula: $A_0 = [W \times 10^3]/[\rho \times l]$.

A density of 0.862 grams/cm³ is used for all specimens.

1-5. Hysteresis Test

The instrument is set up and the specimen is mounted as described in the Tensile Test Setup section above. Data acquisition rate is set to at least 50 Hertz.

The Hysteresis Test method for film specimens involves the following steps (all strains are strains):

(1) Strain the specimen to 130% strain at a constant crosshead speed of 25.4 cm per minute.
(2) Hold specimen at 130% strain for 30 seconds.
(3) Go to 0% strain at a constant crosshead speed of 25.4 cm per minute.
(4) Hold specimen for 1 minute at 0% strain.
(5) Pull the specimen to 0.127 N force and return to 0% strain with no hold time.

The measured and recorded forces, in Newtons (N), are the load force at 75% strain in step (1) and the unload force at 75% strain in step (3). Specimen length at 0.127 N force in step (5) is also recorded and used to calculate the % set in the material as below.

% Set=((Length at 0.127 N force−Original Gauge length)/Original Gauge length)×100

The forces are normalized to stress in MPa as follows: Stress=[measured force at given strain, in Newtons]/[Cross-sectional area, in mm²].

Specimen cross-sectional area is calculated as described above in the Initial Tensile method.

Unload stress at 75% strain is reported in MPa, and ratio of load stress/unload stress at 75% strain is reported.

Five specimens of each film set are measured, and the arithmetic average is calculated for each of the recorded hysteresis parameters for set A and Set B. The set with the lower load stress/unload stress ratio is used for determination of all claimed parameters, including % Strain at break, stress at break, and hysteresis unload stress.

2. Thermal Analysis Method

Approximately 3 milligrams of film are enclosed into a DSC (differential scanning calorimetry) pan. The weight of the specimen is recorded to within ±0.1 mg and used for any calculation performed using the information collected from DSC run.

The thermal properties of the specimen are measured by DSC using a DSC Q2000 V23.10 Build 79 from Perkin Elmer, or equivalent instrument. The specimens are analyzed using standard procedures such as outlined in ASTM D3418-08. This method is capable of determining the temperature ranges over which phase changes occur, e.g., glass transition or crystalline melting. The procedure is modified as follows to carry out two heating cycles.

1: Equilibrate at −90.00° C. for 5 min
2: Ramp up at 20.00° C./min to 200.00° C.
3: Isothermal for 5.00 min
4: Ramp down at 20.00° C./min to −90.00° C.
5: Isothermal for 5.00 min
6: Ramp up at 20.00° C./min to 200.00° C.

The heat flow data collected are used for analyzing crystallinity of the material. The first heat curve (step 2 above) data are used for the calculation of heat of fusion using the method described below.

Figure 2A:
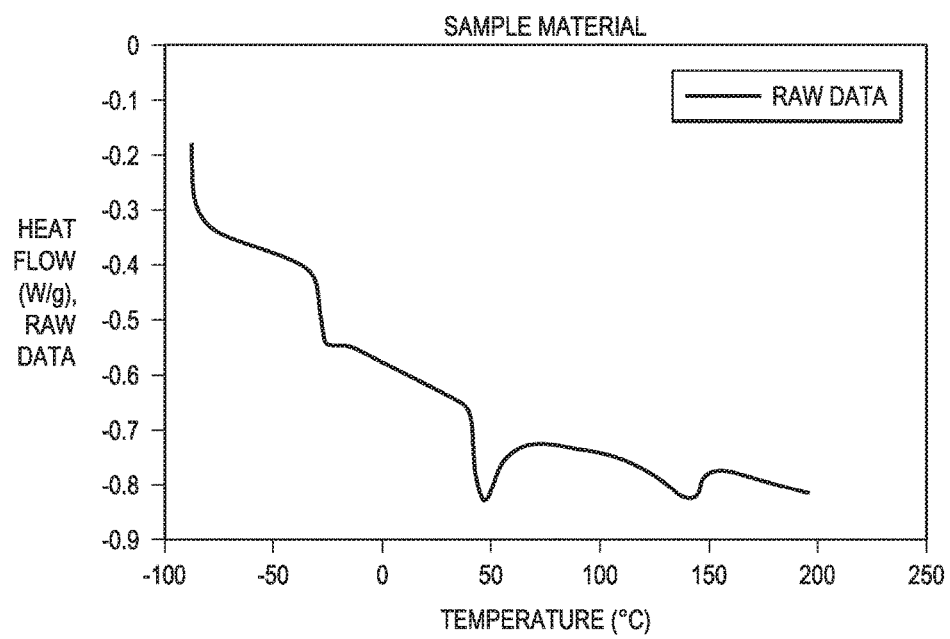
FIG. 2(a)-(d) are systematic representations of the data correction method for the Thermal Analysis Method defined herein.
Figure 2B:
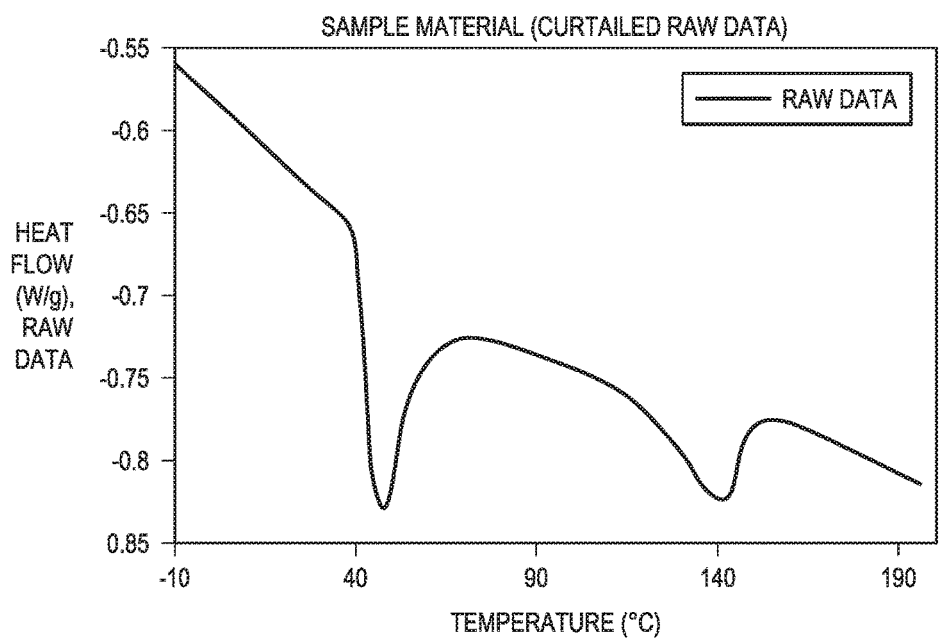

In order to determine accurate heat flow, a mathematical baseline subtraction is performed using $3^{rd}$ order polynomial baseline fit. First the raw data from DSC, heat flow in W/g versus temperature (° C.), is obtained in Microsoft Excel format. The data are then curtailed to a useful temperature range of −10° C. to 200° C., and Heat Flow (W/g) is plotted as a function of Temperature (See FIGS. 2a and 2b).

Figure 2C:
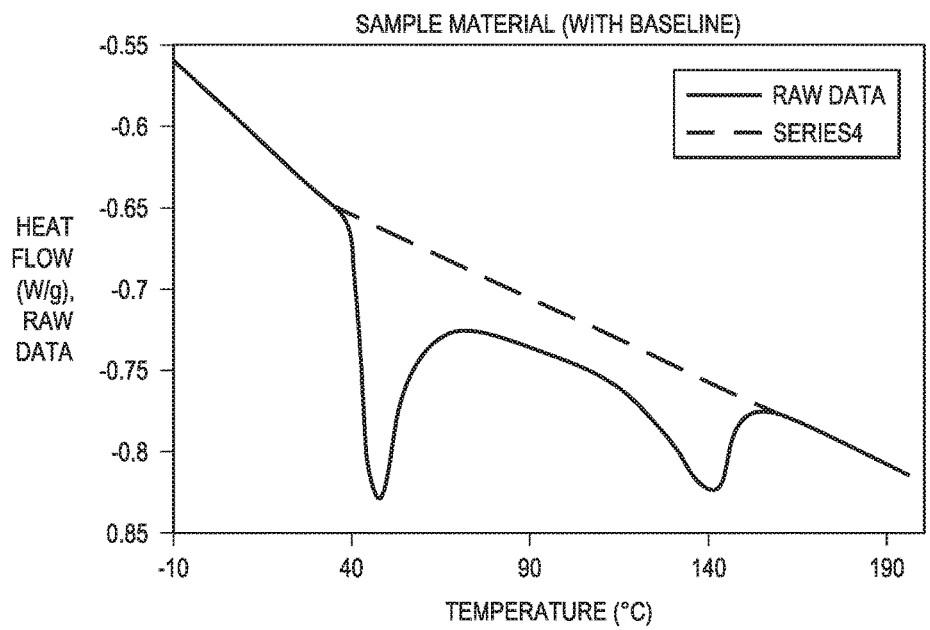
Figure 2D:
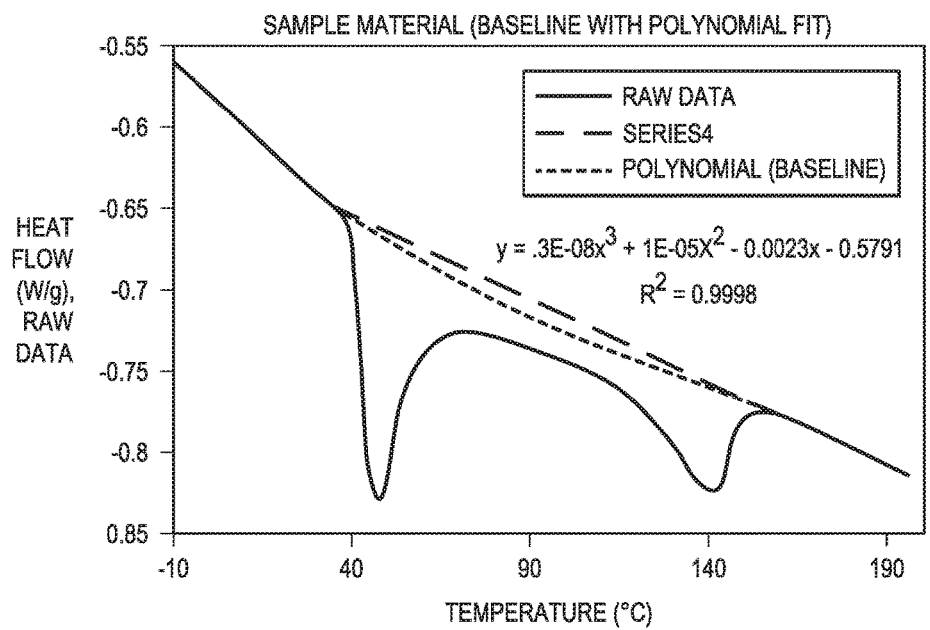

A single $3^{rd}$ order Polynomial curve is fitted to the data from −10° C. to +35° C., and from 165° C. to 200° C. using Microsoft Excel Trendline tool (See FIGS. 2c and 2d). The polynomial curve drawn is selected as the baseline for correction.

Figure 3A:
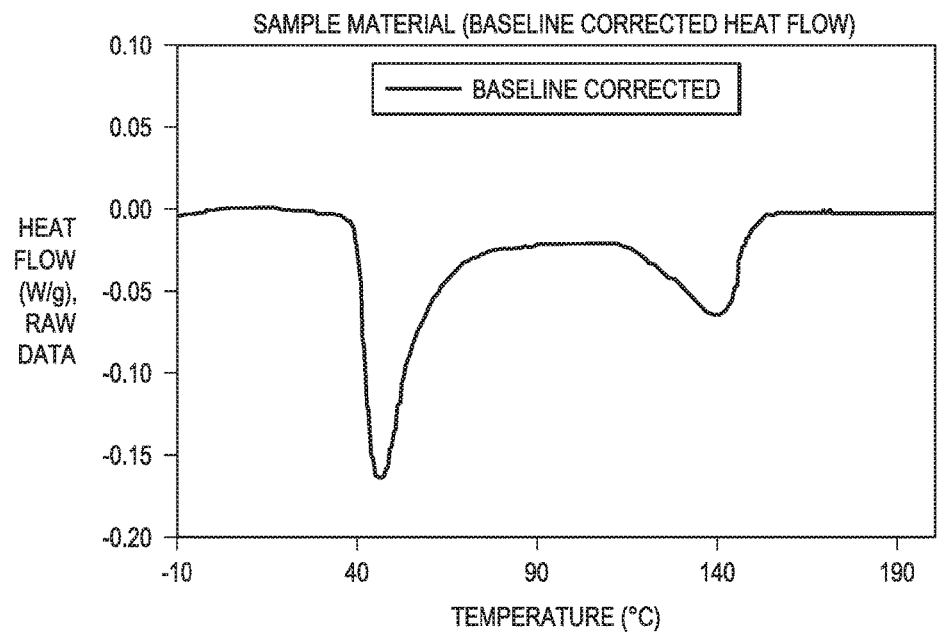
FIG. 3(a)-(b) describe an embodiment of the base line corrected DSC chart according to the Thermal Analysis Method defined herein of an elastomer composition of the present invention.
Figure 3B:
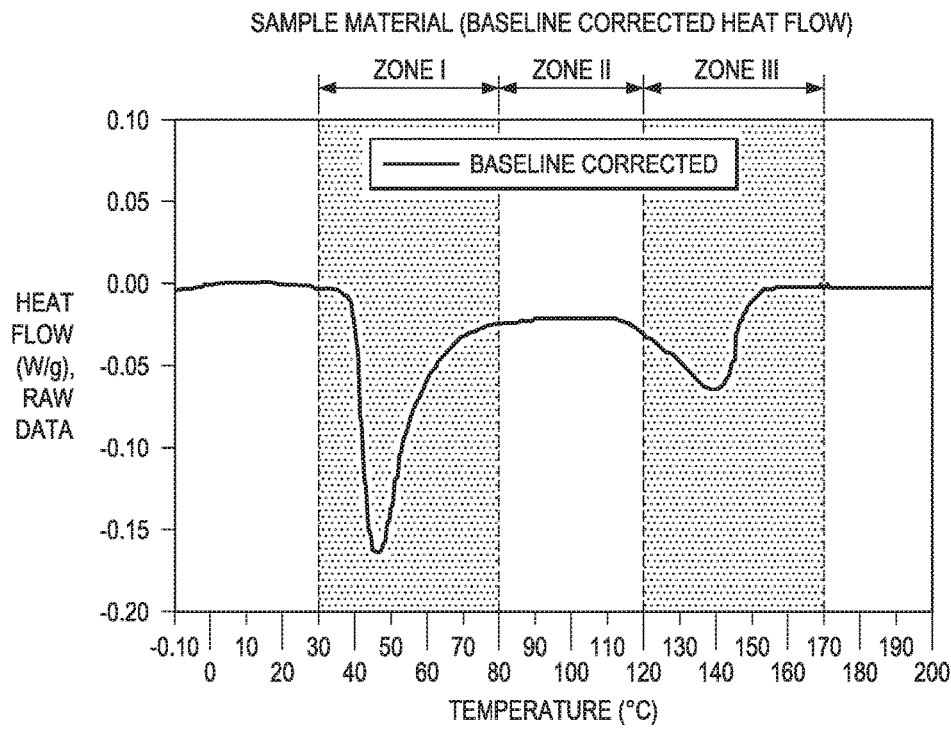
Figure 4A:
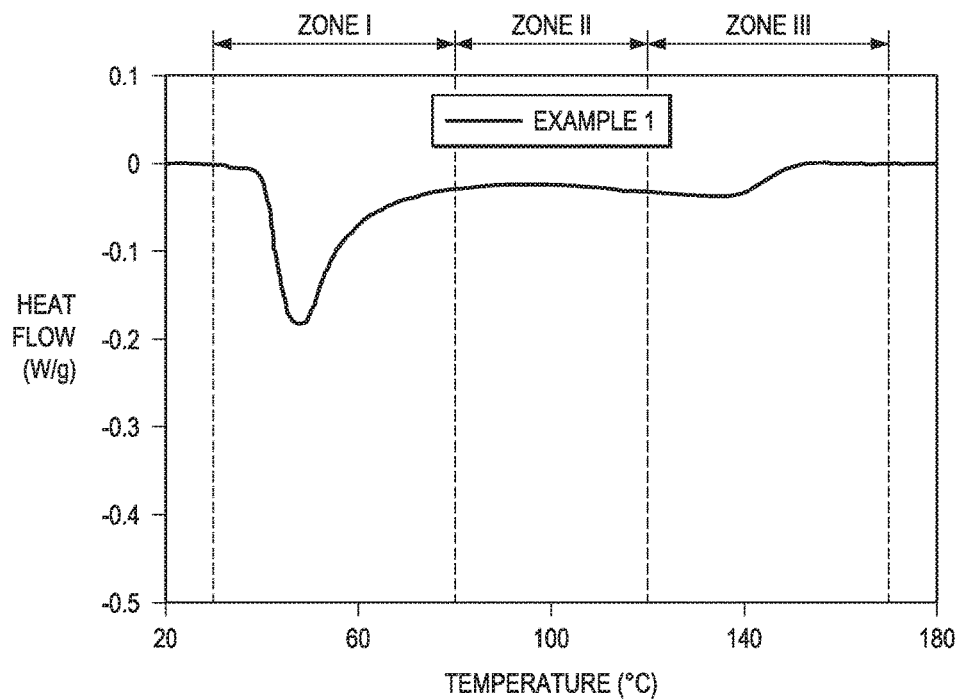
FIG. 4(a)-(h) are the base line corrected DSC charts according to the Thermal Analysis Method defined herein of Examples 1 to 8.
Figure 4B:
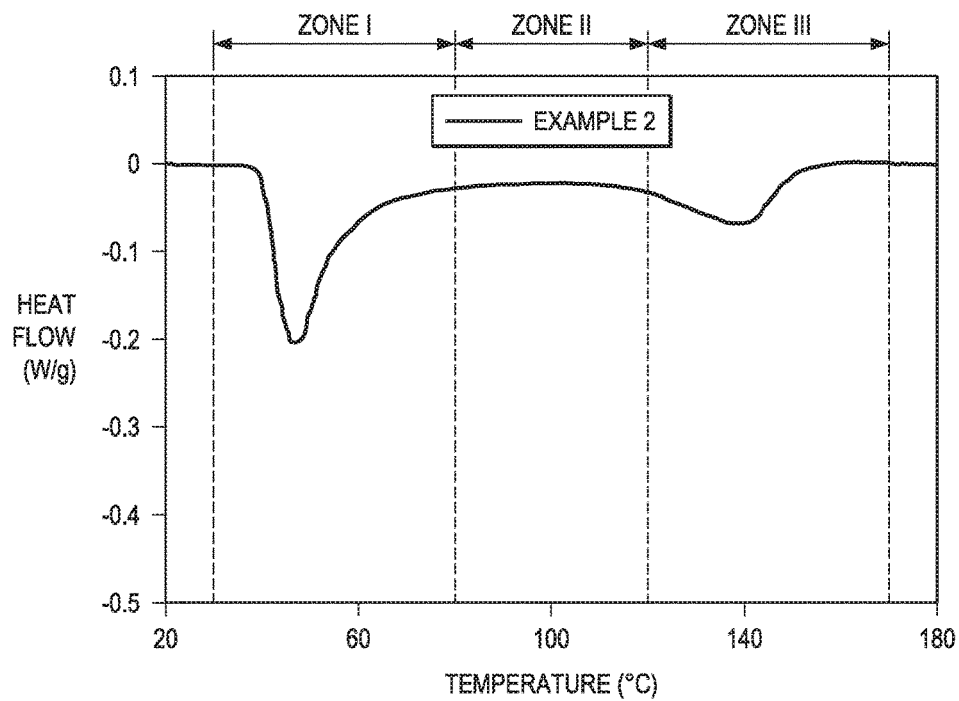
Figure 4C:
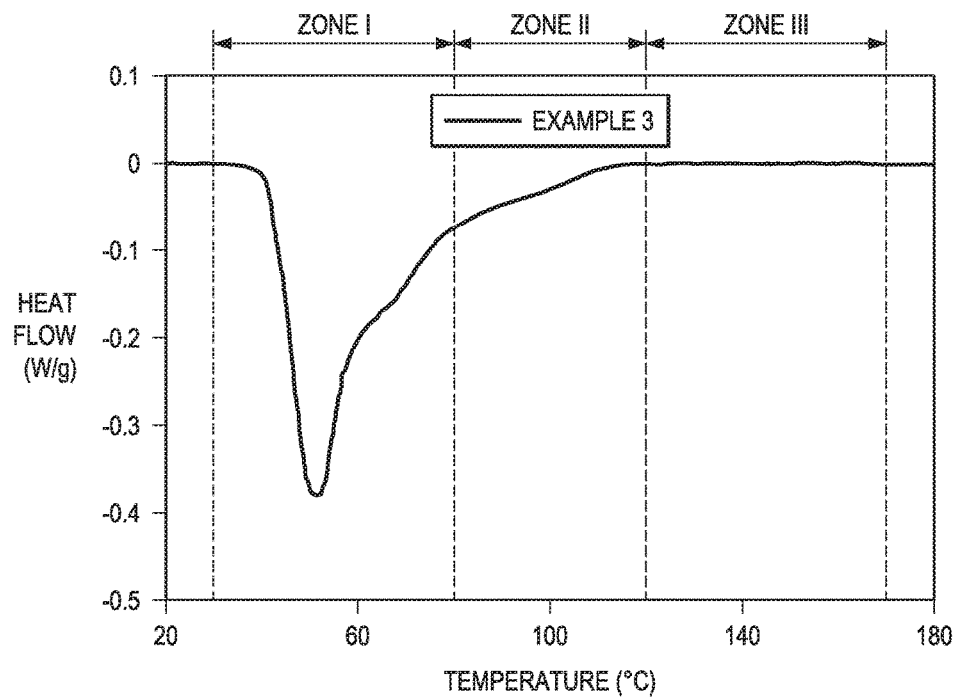
Figure 4D:
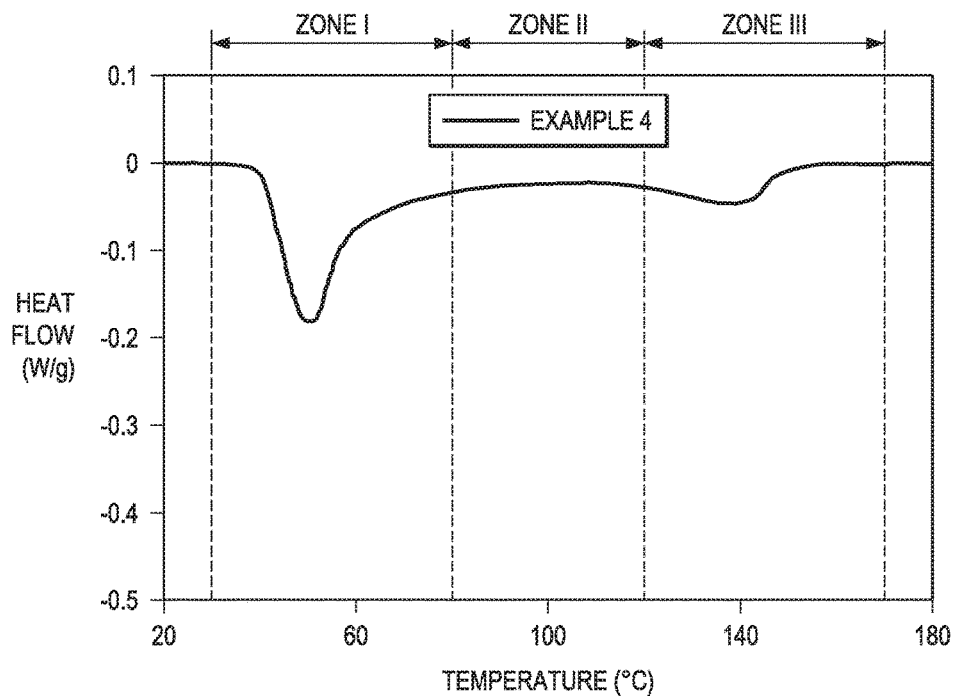
Figure 4E:
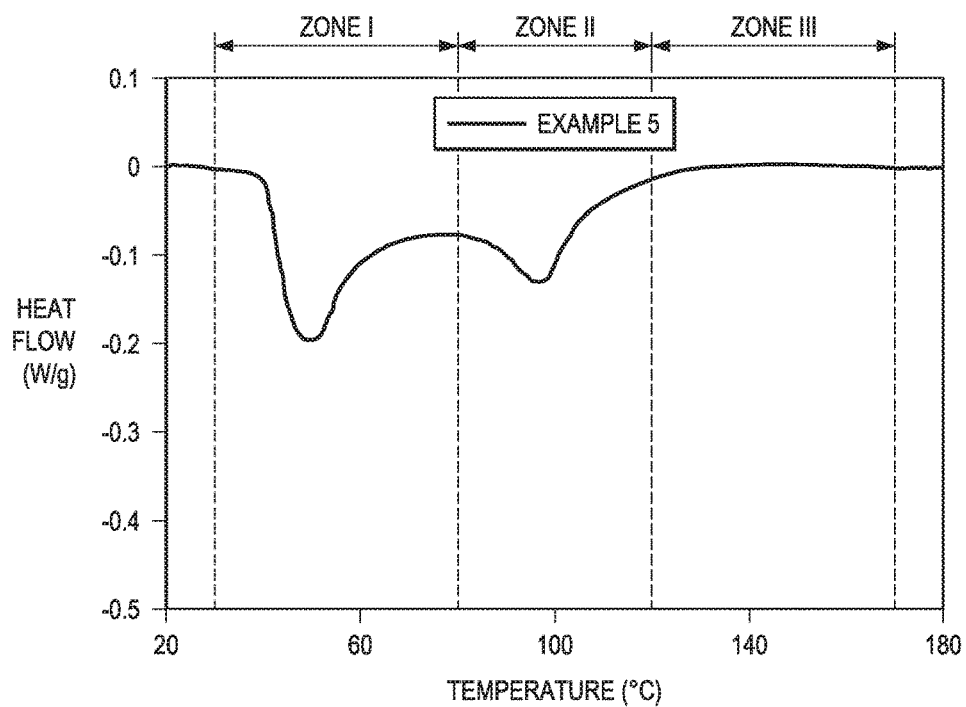
Figure 4F:
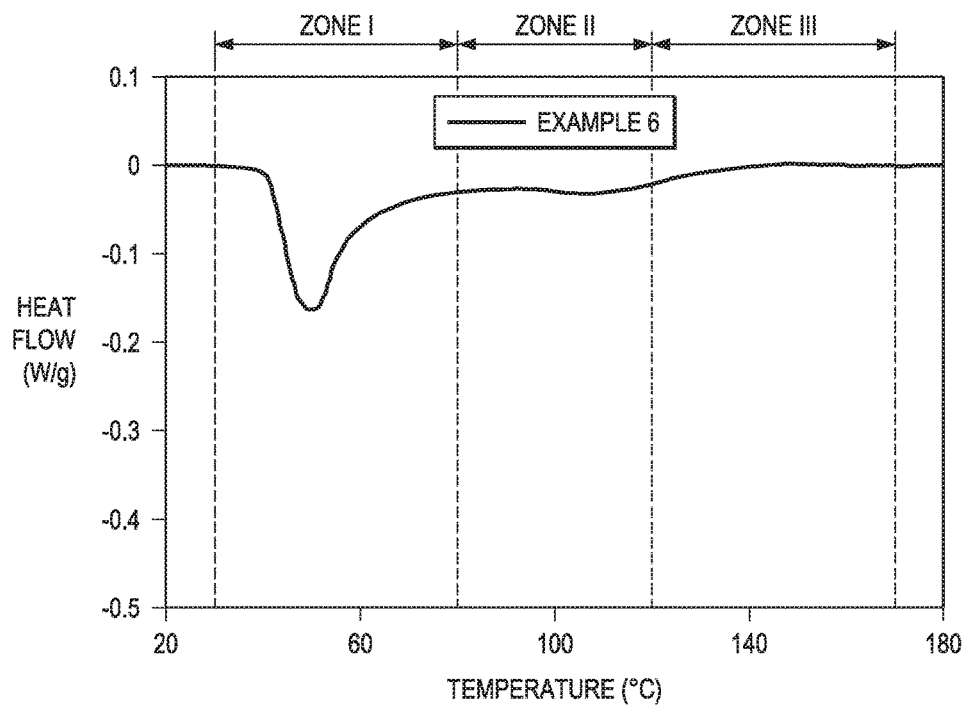
Figure 4G:
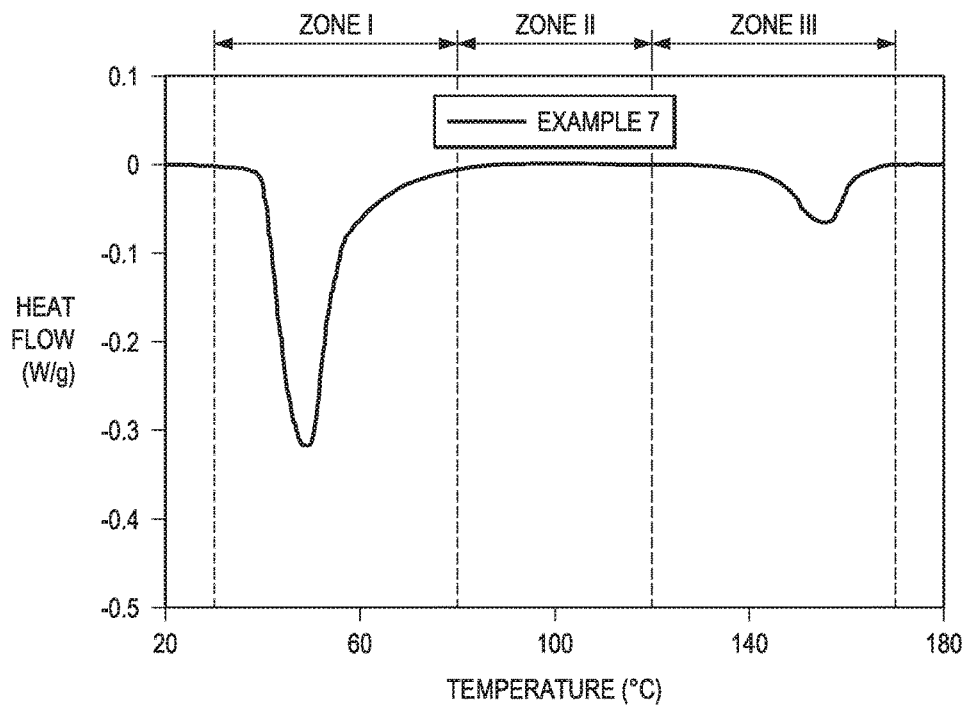
Figure 4H:
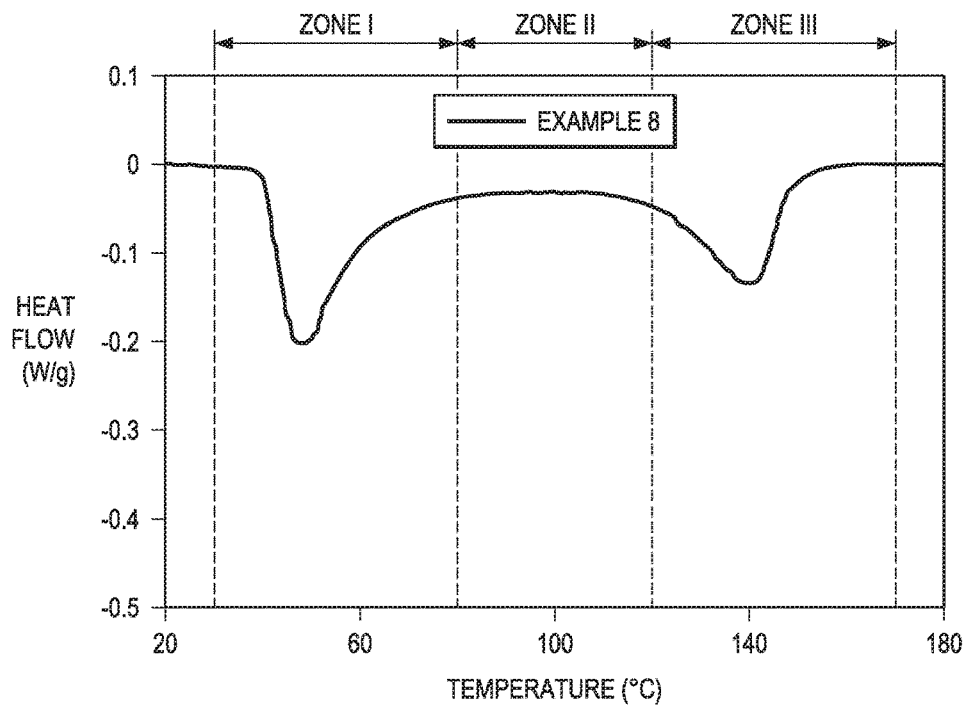

To obtain accurate heat of fusion (enthalpy) data, the polynomial baseline is subtracted from the heat flow curve between −10° C. and 200° C. This is done by calculating the appropriate heat flow baseline value at each data point and subtracting this value from the original heat flow value measured. This shifts the heat flow curve towards zero heat flux line (See FIG. 3a). Once the baseline corrected heat flow data are generated, the plot is divided into three zones (See FIG. 3b): Zone I (30-80° C.), Zone II (80-120° C.), and Zone III (120-170° C.).

The area under corrected heat flow curve is integrated with respect to time to determine the enthalpies in J/g for each of the three temperature zones. The sum of the integrated enthalpy values from Zones I and III, and the ratio of the integrated enthalpy value of Zone I to the value for Zone III are calculated. Two specimens are run and the average integrated enthalpy for each zone is calculated. Average value for each zone is used to calculate and report average integrated enthalpy sum and average integrated enthalpy ratio.

Along with crystalline enthalpy, crystalline melting temperature of a polymer is measured using DSC method described above. Crystalline melting point is defined as in the DSC method ASTM D3418-08, which refers to it as $T_p m$.

3. Air Permeability Test

The air permeability of a substrate (e.g., film, laminate, or article component) is determined by measuring the flow rate of standard conditioned air through a test specimen driven by a specified pressure drop. This test is particularly suited to materials having relatively high permeability to gases, such as nonwovens, apertured films and the like. ASTM D737 is used, modified as follows.

A TexTest FX 3300 instrument or equivalent is used, available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The test pressure drop is set to 125 Pascal and the 5 cm² area test head (model FX 3300-5) or equivalent is used. The result is recorded to three significant digits. The average of 5 specimens is calculated and reported as the Air Permeability Value ($m^3/m^2/min$).

EXAMPLES

Polyolefin elastomers coded A to G, a styrenic block copolymer coded H, and elastomer compositions coded Examples 1-10 made by blending the polyolefin elastomers A to G, were subjected to Tests 1-4 as follows, and reported in Table 1 below. The compositions of the polyolefin elastomers A to G are detailed below. All samples except Example H were provided as a film having a basis weight of 40 gsm.

Test 1: Average integrated enthalpy sum (J/gm) according to the Thermal Analysis Method defined herein, DSC charts for Examples 1 to 8 shown as FIGS. 4(a) to 4(h).

Test 2: Average integrated enthalpy ratio according to the Thermal Analysis Method defined herein.

Test 3: Unload stress at 75% strain above 0.8 MPa according to the Hysteresis Test defined herein.

Test 4: Load stress/unload stress ratio at 75% strain of 1 to 2.6 according to the Hysteresis Test defined herein.

A: Vistamaxx 6102 (available from ExxonMobil, Houston, Tex.): blend of two random propylene-ethylene copolymers exhibiting a single sharp glass transition temperature (Tg) of about −32° C. and an overall crystallinity of about 6 wt %. The crystalline phase exhibits two melting peaks at about 50° C. and about 110° C.

B: NOTIO PN-0040 (available from Mitsui Chemicals, Tokyo Japan): elastic polyolefin resin with glass transition temperature of about −30° C. exhibiting two melting peaks at about 45° C. and about 157° C.

C: L-MODU X901S (available from Mitsui Chemicals, Tokyo Japan): stereo copolymer of polypropylene with a Tg of about −5° C. and a crystallinity of about 13 wt %, exhibiting two melting peaks at about 50° C. and about 68° C.

D: Versify 2400A (available from Dow Chemical, Midland, Mich.): random copolymers of propylene with ethylene with glass transition temperature of about −40° C. with crystalline phase having two melting peaks at about 50° C. and about 140° C.

E: Versify 2400B (available from Dow Chemical, Midland, Mich.): random copolymers of propylene with ethylene with glass transition temperature of about −40° C. with crystalline phase having two melting peaks at about 50° C. and about 140° C.

F: Versify 3401A (available from Dow Chemical, Midland, Mich.): random copolymers of propylene with ethylene with glass transition temperature of about −40° C., having a Crystalline phase with two melting peaks at about 50° C. and about 95° C.

G: Versify 3401B (available from Dow Chemical, Midland, Mich.): random copolymers of propylene with ethylene with glass transition temperature of about −40° C. with crystalline phase having two melting peaks at about 50° C. and about 140° C.

H: Styrenic Copolymer blend made with hydrogenated Styrenic block copolymer, having a film basis weight (gsm) of 78.4. This material is known to have favorable hysteresis performance, while being cost adding.

An Extruder manufactured by Berstorff (a division of KraussMaffei Corporation, Florence, Ky.) under the name ZE25 is used to create sample films of Examples A-H and 1-10. This extruder has 25 millimeter screw diameters, a length-to-diameter ratio of 32, and six heating/cooling barrel zones along its length in addition to a cooled feeding zone. A dry blend of the polyolefin elastomers and any other materials, if required, are tumbled to achieve a relatively uniform mixture, and the dry blend is fed to the extruder via a vibratory gravity feeder. The first heating/cooling zone (barrel zone 2) is maintained at a sufficiently high temperature to initiate softening of the polyolefin elastomers, and consists of conveying elements for transporting the materials forward. The second through fourth heating/cooling zones (barrel zones 3-5) are each equipped with a high shearing forward kneading element and forward conveying elements, while the fourth heating/cooling zone (barrel zone 5) is also equipped with a high shearing backward kneading element and the fifth heating/cooling zone (barrel zone 6) is equipped with a dispersion element and a reverse conveying seal element, all to facilitate increased pressure, shearing, and mixing of the low and high molecular weight components. The sixth and last heating/cooling zone (barrel zone 7) is equipped with forward conveying elements intended to build sufficient pressure behind a cast film die, and to facilitate extrusion through the die. For sample films 1 through 10 in Table 1, the set temperature profile (barrel zones 2-7, transfer tube, die) is about 193° C., 204° C., 216° C., 232° C., 238° C., 249° C., with the screws being rotated at about 50 revolutions per minute. The extrusion die temperature after zone 7 is set at 249° C. For sample film H, the set temperature profile (barrel zones 2-7, transfer tube, die) is about 220° C., 230° C., 230° C., 230° C., 230° C., 230° C., 230° C., 230° C., with the screws being rotated at about 50 revolutions per minute. A 25.4 cm wide coat hanger cast film die is used to shape the material into a thin film, and a film take-off unit is positioned to receive the extrudate which is collected on double sided silicone coated release paper and wound onto a cardboard roll. An air knife (Curtain Transvector® Air knife Model 921-12) at 275 kPa and at room temperature was used in between the die and take-off roll to cool down the material and to help with web handling/winding. The film basis weight is adjusted by varying the linear speed of the take-off unit. For generating data herein, a mono-layer film of the material is collected from the 254 mm cast film die, and the middle 127 mm is used. The film is stored at room temperature (22±2° C.) and allowed to crystallize for 3 to 6 weeks at room temperature to reach equilibrium.

Stress at break and % Strain at break of the sample films are measured in cross machine direction using the Initial Tensile Test. They are reported in Table 2 below.

Pre-Straining and aging is conducted as follows: The extruded film is pre-strained in cross machine direction to simulate the activation process used in the production of elastic members useful for absorbent articles. The film is pre-strained to 300% strain using tensile tester at 0.166 s$^{-1}$ strain rate and immediately returned to zero strain at 0.166 s$^{-1}$. The ratio of initial gauge length to width of the sample is set to 1. The pre-strained film is then removed from the tensile tester and laid flat on a smooth surface. It is aged at 22±2° C. for 3-6 weeks to reach equilibrium. The film is analyzed by the Thermal Analysis Method and the Hysteresis Test as detailed above.

TABLE 1

| Example | Composition and weight percentage | Test 1 (J/gm) | Test 2 | Test 3 (MPa) | Test 4 |
|---|---|---|---|---|---|
| A | 100% A | 8.97 | >1000 | 1.0 | 1.94 |
| B | 100% B | 24.45 | 3.49 | 0.87 | 3.78 |
| C | 100% C | 31.39 | >1000 | 0.86 | 6.94 |
| D | 100% D | 11.00 | 8.85 | 0.77 | 2.08 |
| E | 100% E | | | 1.44 | 3.02 |
| F | 100% F | | | 0.97 | 2.63 |
| G | 100% G | | | 1.00 | 4.33 |
| H | 100% H | | | 0.71 | 1.09 |
| 1 | 40% A, 36% E, 24% G | 13.07 | 3.64 | 1.28 | 2.13 |
| 2 | 40% A, 60% E | 15.35 | 2.19 | 1.29 | 2.30 |
| 3 | 40% A, 60% C | 21.69 | >1000 | 1.00 | 3.44 |
| 4 | 80% D, 20% E | 14.52 | 3.11 | 1.03 | 2.15 |
| 5 | 40% A, 60% F | 13.77 | 193.78 | 1.02 | 2.19 |
| 6 | 40% A, 60% D | 9.69 | 13.36 | 0.97 | 1.98 |
| 7 | 40% A, 60% B | 15.28 | 4.89 | 1.03 | 2.56 |
| 8 | 60% E, 40% G | 19.44 | 1.49 | 1.31 | 3.36 |
| 9 | 20% A, 48% E, 32% G | | | 1.28 | 2.9 |
| 10 | 20% A, 80% C | | | 0.78 | 5.0 |

Examples 1-2 and 4-7 provided suitable hysteresis properties, and are expected to provide good performance when used as stretch elements for absorbent articles.

TABLE 2

| Example | Stress at Break (MPa) | % Strain at Break (%) |
|---|---|---|
| 1 | 24.4 | 798 |
| 2 | 21.4 | 740 |
| 4 | 13.0 | 750 |

Examples 1, 2, and 4 provided suitable robustness to tensile stress, and are expected to provide good performance during processing for use as stretch elements for absorbent articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An elastomer composition comprising a polyolefin elastomer material, the elastomer composition having the following properties:
   (1) an average integrated enthalpy sum from 5 J/g to 17 J/g;
   (2) an average integrated enthalpy ratio of from 0.6 to 300; and
   (3) a load stress/unload stress ratio at 75% strain of 1 to 2.6.

2. An elastomer composition comprising a polyolefin elastomer material, the elastomer composition having the following properties after having been pre-strained to 300% strain and aged for 3 weeks:
   (1) an average integrated enthalpy value from 5 J/g to 17 J/g, wherein the value of temperature zones between 30-80° C. and 120-170° C. are added;
   (2) an average integrated enthalpy ratio of from 0.6 to 300, when comparing the value of temperature zone between 30-80° C. to value of temperature zone between 120-170° C.; and
   (3) a load stress/unload stress ratio at 75% strain of 1 to 2.6.

3. The elastomer composition of claim 1, wherein the elastomer composition is prepared by extrusion blending at least 2 polyolefin elastomers.

4. The elastomer composition of claim 3, wherein at least one of the at least 2 polyolefin elastomers has a crystalline melting point of at least 75° C.

5. The elastomer composition of claim 3, wherein at least one of the at least 2 polyolefin elastomers comprises a metallocene polyolefin.

6. The elastomer composition of claim 1 having a crystalline melting point of at least 75° C.

7. The elastomer composition of claim 1 having a stress at break of at least 10 MPa.

8. The elastomer composition of claim 1 having a % Strain at break of at least 500%.

9. The elastomer composition of claim 1, wherein the elastomer composition has an unload stress at 75% strain of above 0.8 MPa.

10. The elastomer composition of claim 1, further comprising a bacteriostat.

11. The elastomer composition of claim 1, further comprising a processing aid selected from the group consisting of synthetic and natural oils; hydrogenated synthetic and hydrogenated natural oils; naphthenic oils; paraffinic oils; olefin oligomers; vegetable oils; animal oils; petroleum derived waxes; and mixtures thereof.

12. An elastic film made of the composition of claim 1 having a basis weight of from about 5 to about 150 g/m$^2$.

13. The elastic film of claim 12 wherein the film is breathable.

14. A multi-layer laminate comprising the elastic film of claim 12.

15. The multi-layer laminate of claim 14, wherein the multi-layer laminate comprises one or more skin layers, wherein at least one of the one or more skin layers comprises a plastically extensible material.

16. The multi-layer laminate of claim 14, wherein the multi-layer laminate comprises one or more skin layers, wherein at least one of the one or more skin layers comprises an elastic material.

17. A component for an absorbent article made of the elastic film of claim 12, wherein the component is selected from the group consisting of waistbands, leg elastic, side panels, elastic belts, stretch outer cover, and stretch ears.

18. The elastomer composition of claim 2, wherein the elastomer composition is prepared by extrusion blending at least 2 polyolefin elastomers, wherein at least one of the at least 2 polyolefin elastomers has a crystalline melting point of at least 75° C., and wherein at least one of the at least 2 polyolefin elastomers comprises an elastomeric polypropylene.

19. The elastomer composition of claim 2 having a crystalline melting point of at least 75° C.

20. An elastic film comprising the elastomer composition of claim 2 having a basis weight of from about 5 to about 150 g/m$^2$, wherein the elastic film is breathable.

* * * * *